United States Patent [19]
Pavkovich

[11] Patent Number: 6,093,183
[45] Date of Patent: Jul. 25, 2000

[54] SAFETY INTRAVENOUS CONNECTOR

[76] Inventor: Mary Pavkovich, 6534 N. Sacramento Ave., Chicago, Ill. 60645

[21] Appl. No.: 09/353,745

[22] Filed: Jul. 14, 1999

Related U.S. Application Data

[63] Continuation-in-part of application No. 09/131,072, Aug. 7, 1998, abandoned.

[51] Int. Cl.$^7$ .................................................. A61M 25/16
[52] U.S. Cl. .......................................... 604/539; 604/533
[58] Field of Search ................................... 604/283, 280, 604/263, 256, 905, 411, 412, 192, 197–198, 523, 533–535, 539, 272

[56] References Cited

U.S. PATENT DOCUMENTS

| | | | |
|---|---|---|---|
| 4,950,260 | 8/1990 | Bonaldo | 604/283 |
| 4,964,855 | 10/1990 | Todd et al. | 604/283 |
| 4,998,925 | 3/1991 | Al-Sioufi et al. | 604/283 |
| 5,057,093 | 10/1991 | Clegg et al. | 604/283 |
| 5,067,950 | 11/1991 | Broadnax et al. | 604/411 |
| 5,122,123 | 6/1992 | Vaillancourt | 604/192 |
| 5,281,206 | 1/1994 | Lopez | 604/283 |
| 5,344,414 | 9/1994 | Lopez et al. | 604/283 |
| 5,423,775 | 6/1995 | Cannon | 604/283 |
| 5,688,254 | 11/1997 | Lopez et al. | 604/905 |
| 5,738,663 | 4/1998 | Lopez | 604/249 |
| 5,776,116 | 7/1998 | Lopez at al. | 604/283 |
| 5,785,693 | 7/1998 | Haining | 604/249 |
| 5,893,397 | 4/1999 | Peterson at al. | 604/411 |
| 5,931,820 | 8/1999 | Morse | 604/283 |

*Primary Examiner*—Sharon Kennedy
*Attorney, Agent, or Firm*—Goldstein & Canino

[57] ABSTRACT

A safety connector, for connecting a fluid source to an intravenous hub, comprising a main tube having an inner wall having an inside diameter which matches the fluid source and intravenous hub. The main tube has a first end and a second end. A needle extends through the main tube, the needle having a receptacle end and a pointed end. The receptacle end is located at the first end of the main tube to create a fluid connection therewith. The receptacle end is flared toward the second end. The pointed end is slightly recessed from the second end to prevent needle prick injuries when the connector is being handled. The first end of the main tube attaches over a fluid source to create a fluid connection therewith, and the second end attaches over the intravenous hub so that the pointed end of the needle punctures said intravenous hub and thereby completes a fluid connection between the fluid source and the intravenous hub, while the hub becomes wedged upon the receptacle end of the needle, thereby creating a strong physical connection between the hub and connector.

4 Claims, 2 Drawing Sheets

SAFETY INTRAVENOUS CONNECTOR

CROSS REFERENCES AND RELATED SUBJECT MATTER

This application is a continuation-in-part of patent application Ser. No. 09/131,072, filed in the United States Patent Office on Aug. 7, 1998, now abandoned.

BACKGROUND OF THE INVENTION

The invention relates to a safety intravenous connector. More particularly, the invention relates to a connector which has an internal needle for puncturing an IV hub and providing a connection therewith, while avoiding the possibility of a needle prick to the health care professional while making said connection.

With the increased concern about the possibility of contracting blood borne diseases, such as AIDS and hepatitis, from accidental self-inflicted needle stick injuries with a possibly contaminated needle, the health care industry is presently concentrating on minimizing or eliminating the use of needles wherever possible. The FDA has urged health care workers to avoid recapping of needles after using them for intravenous (IV) and intramuscular injections. The current trend is to eliminate possible points of contact between health care professionals and needles.

Needle-less intravenous ports have been proposed in an attempt at eliminating the need for needles during certain IV procedures. For example, U.S. Pat. No. 4,950,260 to Bonaldo discloses a medical connector which uses a tubular needle, and accordingly requires both male and female components to make a connection. While these units may be suitable for the particular purpose employed, or for general use, they would not be as suitable for the purposes of the present invention as disclosed hereafter.

SUMMARY OF THE INVENTION

It is an object of the invention to produce a safety connector which attaches onto any standard intravenous device, and provides a fluid connection thereto.

It is another object of the invention that the possibility of needle-prick injuries during the connection is eliminated. Accordingly, the needle point is located at a recessed position from the connector second end, so that it is not possible for the needle point to come into contact with the skin of the health care professional while the connector is being used.

It is a still further object of the invention to provide a safety connector which is a one piece construction, and thereby eliminates the necessity for a two piece connector.

The invention is a safety connector, for connecting a fluid source to an intravenous hub, comprising a main tube having an inner wall having an inside diameter which matches the fluid source and intravenous hub. The main tube has a first end and a second end. A needle extends through the main tube, the needle having a receptacle end and a pointed end. The receptacle end is located at the first end of the main tube to create a fluid connection therewith. The receptacle end is flared toward the second end. The pointed end is slightly recessed from the second end to prevent needle prick injuries when the connector is being handled. The first end of the main tube attaches over a fluid source to create a fluid connection therewith, and the second end attaches over the intravenous hub so that the pointed end of the needle punctures said intravenous hub and thereby completes a fluid connection between the fluid source and the intravenous hub, while the hub becomes wedged upon the receptacle end of the needle, thereby creating a strong physical connection between the hub and connector.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
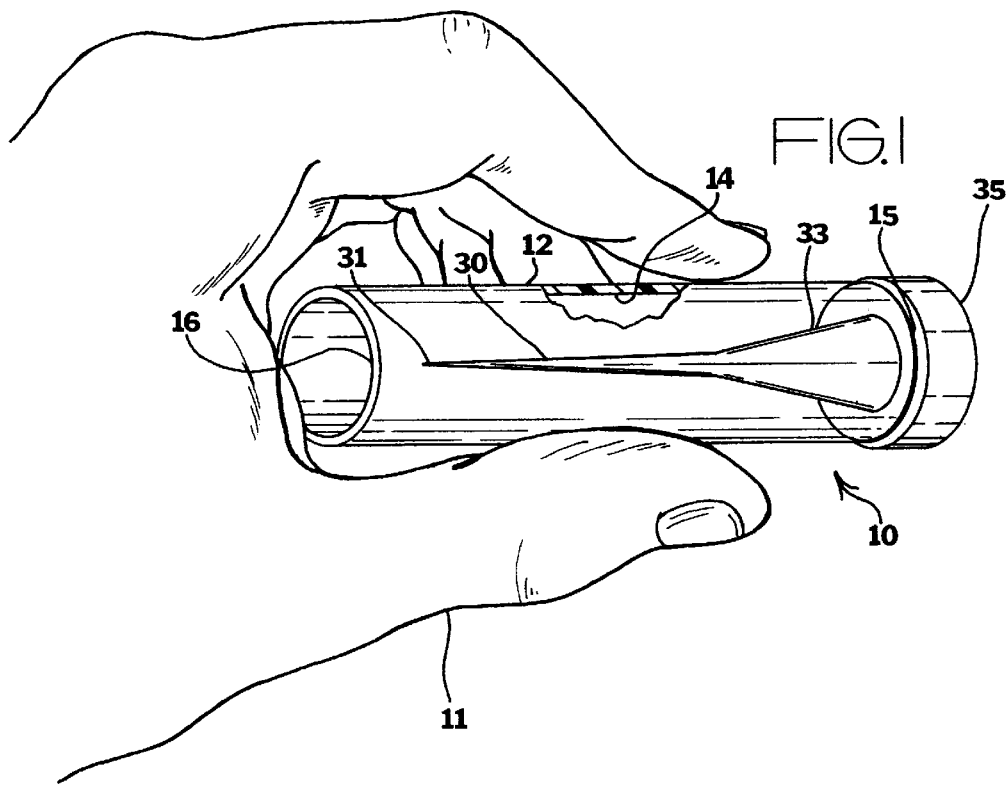
FIG. 1 is a diagrammatic perspective view, illustrating the safety connector per se, wherein said safety connector is held by a human hand.

FIG. 1 illustrates a safety connector 10, being held against a human hand 11. The safety connector has a main tube 12 having an inner wall 14 which has an inside diameter that is compatible with existing intravenous tubing. The main tube 12 has a first end 15 and a second end 16. A needle 30 extends within the main tube 12. The needle 30 has a pointed end 31 and a receptacle end 33. The receptacle end 33 is in fluid communication with the first end 15 of the main tube 12. The first end 15 is covered with a cap 35 prior to use.

The pointed end 31 of the needle 30 is located near the second end 16 of the main tube 12 but is recessed slightly from said second end 16 so that the pointed end 31 of the needle 30 cannot puncture the skin of the hand 11.

Figure 2:
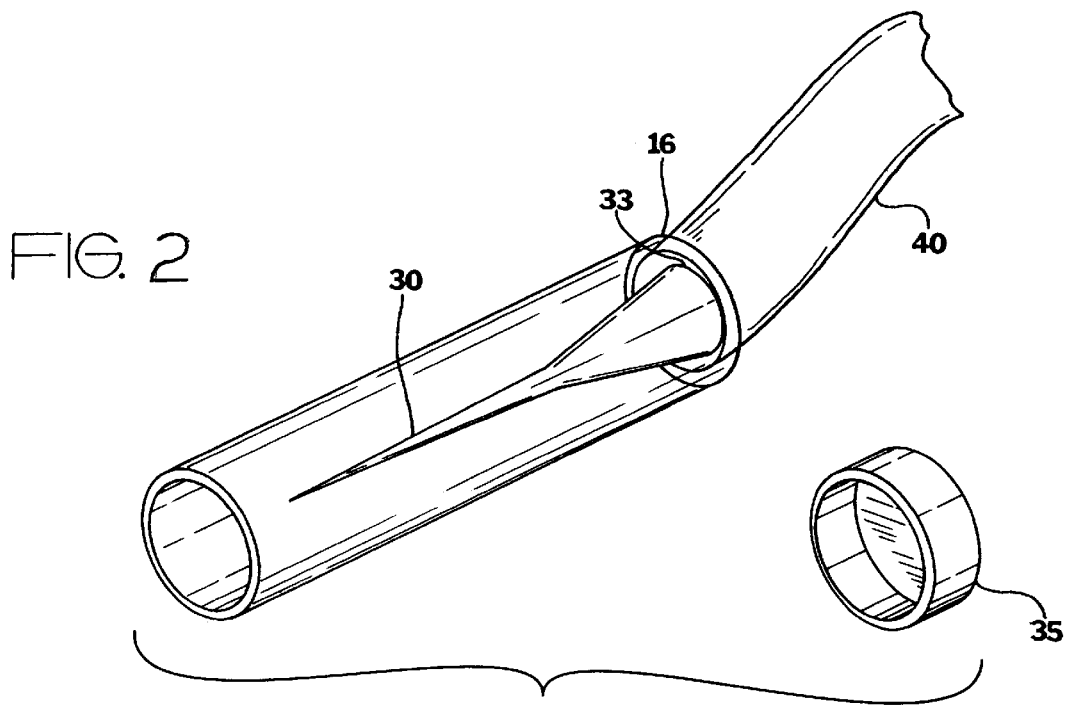
FIG. 2 is a diagrammatic perspective view, wherein the cap has been removed from the connector and the first end thereof has been attached to a fluid source.

In FIG. 2, the cap 35 has been removed, and a fluid source is inserted into the second end 16, thus providing a fluid connection between the fluid source 40 and the receptacle end 33 of the needle 30.

Figure 3:
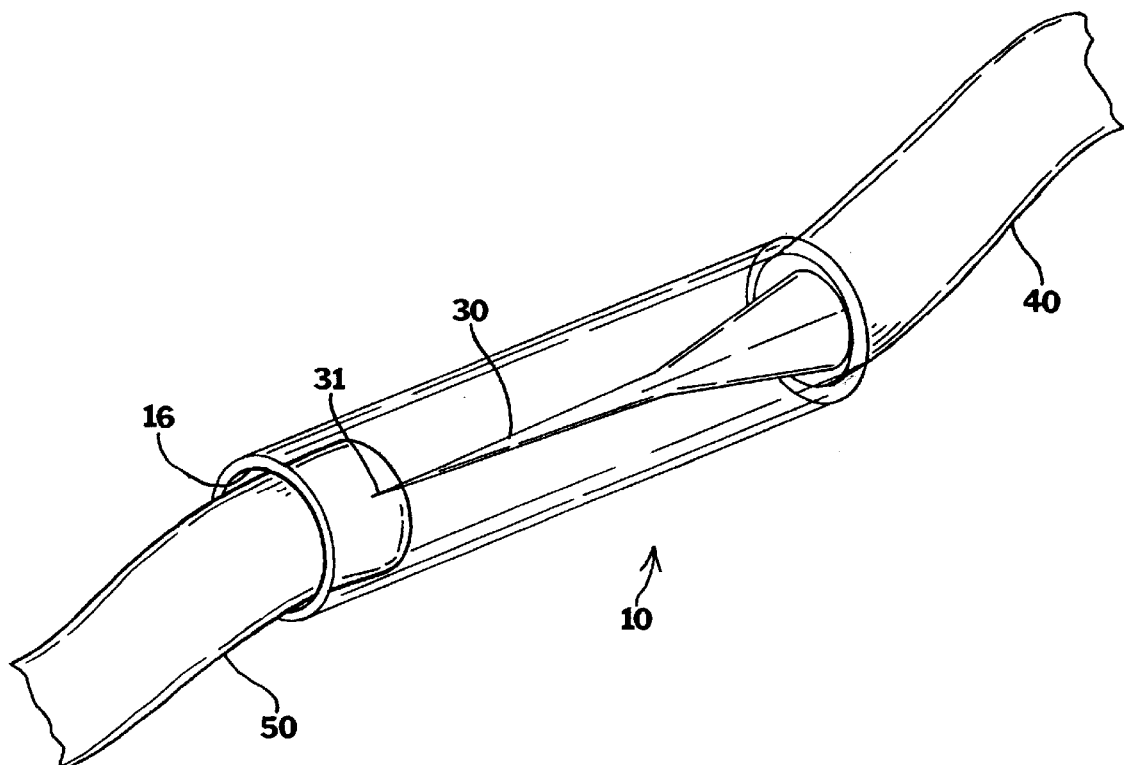
FIG. 3 is a diagrammatic perspective view, wherein the second end has been attached over an intravenous tube hub so that the needle penetrates the hub and creates a fluid connection therewith.

In FIG. 3, the connector 10 has been attached onto a intravenous hub 50 by extending the hub 50 into the second end 16 until the pointed end 31 of the needle 30 punctures the hub 50. A fluid connection is thereby created between the fluid source 40 and the intravenous hub 50, through the connector 10. At no point was the health care professional creating the connection under any risk of receiving a needle prick injury.

As illustrated in FIG. 1, the receptacle end 33 is flared toward the first end 15. This flaring of the receptacle end 33 acts to allow secure attachment of the hub 50 into the second end 16. The flared receptacle end 33 also serves to act as a limit stop for the hub 50, and the inclined plane effect thereof serves to wedge the hub 50 onto the needle 30. Thus, the needle serves the dual purposes of making a fluid connection with the hub 50, and holding the hub securely onto the needle 30 without requiring additional connectors, clasps, locking devices, or the like. Accordingly, the flared receptacle end 33 eliminates the necessity for a two part connector.

In conclusion, herein is presented a safety intravenous connector which is capable of providing a connection between a fluid source and an intravenous hub without at any time exposing the health care professional to a needle, and thereby eliminating the risk of a needle prick injury.

What is claimed is:

1. A safety connector, for connecting a fluid source to an intravenous hub, comprising:

a main tube having a first end and a second end, the main tube has an inner wall which has an inside diameter which is adapted to match the fluid source and the intravenous hub;

a needle having a pointed end and a receptacle end, the receptacle end located near the first end and creating a fluid connection therewith, the pointed end located near the second end but recessed slightly therefrom, the receptacle end being flared toward the second end; and wherein the receptacle end is adapted to attach onto a fluid source and creates a fluid connection with the receptacle end of the needle, and the second end is adapted to extend over the intravenous hub so that the pointed end of the needle punctures the intravenous hub and creates a fluid connection between the fluid source and the intravenous hub, the hub becoming wedged upon the flared receptacle end as the needle is inserted into the hub.

2. The safety connector as recited in claim 1, further comprising a removable cap which is adapted to cover the first end, and be removed just prior to use.

3. A safety connection method for attaching an intravenous hub to a fluid source using a connector having a main tube having a first end and a second end, a needle extending through the main tube having a receptacle end in fluid communication with the first end of the main tube and a pointed end recessed slightly from the second end of the main tube, the receptacle end of the needle being flared toward the second end, comprising the steps of:

extending the first end over the fluid source to create a fluid connection between the receptacle end and the fluid source; and extending the second end over the intravenous hub to puncture the intravenous hub with the pointed end of the needle and create a fluid connection between the fluid source and the intravenous hub and to wedge the hub upon the flare of the receptacle end.

4. The safety connection method as recited in claim 3, wherein the first end is initially covered by a cap, and wherein the method steps as recited are preceded by the step of removing the cap.

\* \* \* \* \*